(12) United States Patent
Tronci et al.

(10) Patent No.: US 10,046,087 B2
(45) Date of Patent: Aug. 14, 2018

(54) COLLAGEN BASED MATERIALS

(71) Applicant: University of Leeds, Leeds (GB)

(72) Inventors: Giuseppe Tronci, Leeds (GB); Stephen John Russell, Leeds (GB); David John Wood, Leeds (GB)

(73) Assignee: University of Leeds, Leeds (GB)

( * ) Notice: Subject to any disclaimer, the term of this patent is extended or adjusted under 35 U.S.C. 154(b) by 46 days.

(21) Appl. No.: 14/778,656

(22) PCT Filed: Mar. 21, 2014

(86) PCT No.: PCT/GB2014/050893
§ 371 (c)(1),
(2) Date: Sep. 21, 2015

(87) PCT Pub. No.: WO2014/147415
PCT Pub. Date: Sep. 25, 2014

(65) Prior Publication Data
US 2016/0051727 A1 Feb. 25, 2016

(30) Foreign Application Priority Data
Mar. 22, 2013 (GB) .................................. 1305281.6

(51) Int. Cl.
| | |
|---|---|
| A61L 15/32 | (2006.01) |
| C08F 289/00 | (2006.01) |
| A61L 27/24 | (2006.01) |
| C08J 3/24 | (2006.01) |
| C08L 89/06 | (2006.01) |
| C08H 1/06 | (2006.01) |
| A61L 15/42 | (2006.01) |
| A61L 15/60 | (2006.01) |
| A61L 27/52 | (2006.01) |
| A61L 27/56 | (2006.01) |
| C08J 3/28 | (2006.01) |

(52) U.S. Cl.
CPC ............. *A61L 27/24* (2013.01); *A61L 15/325* (2013.01); *A61L 15/425* (2013.01); *A61L 15/60* (2013.01); *A61L 27/52* (2013.01); *A61L 27/56* (2013.01); *C08F 289/00* (2013.01); *C08H 1/06* (2013.01); *C08J 3/24* (2013.01); *C08J 3/28* (2013.01); *C08L 89/06* (2013.01); *A61L 2430/00* (2013.01); *C08J 2389/00* (2013.01); *C08J 2389/06* (2013.01)

(58) Field of Classification Search
CPC ...... A61L 15/325; A61L 15/425; A61L 15/60; A61L 27/24; A61L 27/52; A61L 27/56; A61L 2430/00; C08F 289/00; C08H 1/06; C08J 3/24; C08J 3/28; C08J 2389/00; C08J 2389/06; C08L 89/06
See application file for complete search history.

(56) References Cited

U.S. PATENT DOCUMENTS

| | | | |
|---|---|---|---|
| 4,001,442 A * | 1/1977 | Stahlberger | A22C 13/0016 106/156.31 |
| 6,458,386 B1 | 10/2002 | Schacht et al. | |
| 2007/0009585 A1* | 1/2007 | Morinaga | A61L 15/325 424/445 |
| 2012/0220691 A1 | 8/2012 | Shreiber et al. | |

FOREIGN PATENT DOCUMENTS

| | | |
|---|---|---|
| EP | 0444244 A2 | 9/1991 |
| WO | WO2009044053 * | 4/2009 |
| WO | WO2010048281 * | 4/2010 |

OTHER PUBLICATIONS

Brochure Ciba Irgacure 2959, 2008.*
Amudeswari et al., "Hydrogels based on graft copolymers of collagen synthesis," Journal of Applied Polymer Science. 32:4939-44 (1986).
Amudeswari et al., "Short-term biocompatibility studies of hydrogel-grafted collagen copolymers," Journal of Biomedical Materials Research. 20:1103-9 (1986).
Brinkman et al., "Photo-cross-linking of type I collagen gels in the presence of smooth muscle cells: mechanical properties, cell viability, and function," Biomacromolecules. 4:890-5 (2003).
Maier et al., "Study on the crosslink-induced radical intercoupling between atelocollagen and in situ-generated (co) polymers," Scientific Study & Research. 9(2):213-20 (2008).
Nichol et al., "Cell-laden microengineered gelatin methacrylate hydrogels," Biomaterials. 31:5538-44 (2010).
Written Opinion for International Application No. PCT/GB2014/050893, dated Jun. 25, 2014, 10 pages.
International Search Report for PCT/GB2014/050893, dated Jun. 25, 2014, 4 pages.

* cited by examiner

*Primary Examiner* — Irina S Zemel
(74) *Attorney, Agent, or Firm* — Hoffman Warnick LLC

(57) ABSTRACT

There are provided collagen based polymeric materials comprising collagen molecules and/or collagen derived molecules which have been functionalized by the addition of one or more ethylenically unsaturated moieties and which have been cross-linked via said moieties. Also provided are collagen based compositions and methods of producing collagen based polymeric materials.

16 Claims, 2 Drawing Sheets

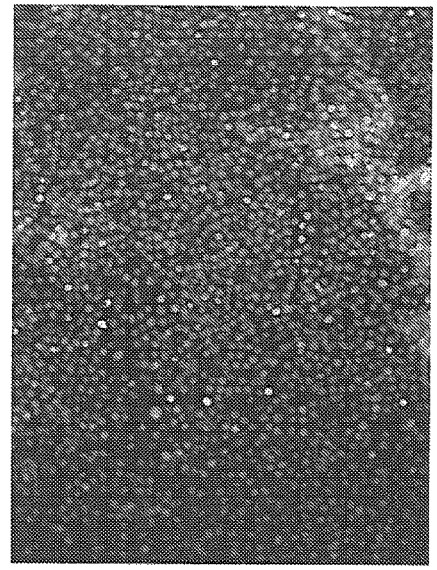
Fig. 5. L929 mouse fibroblasts morphology after 48 hours cell culture on sample extract
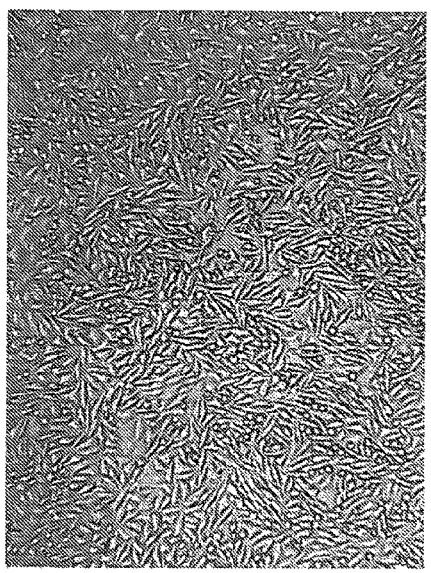
Fig. 6. L929 mouse fibroblasts morphology after 48 hours cell culture on double strength medium
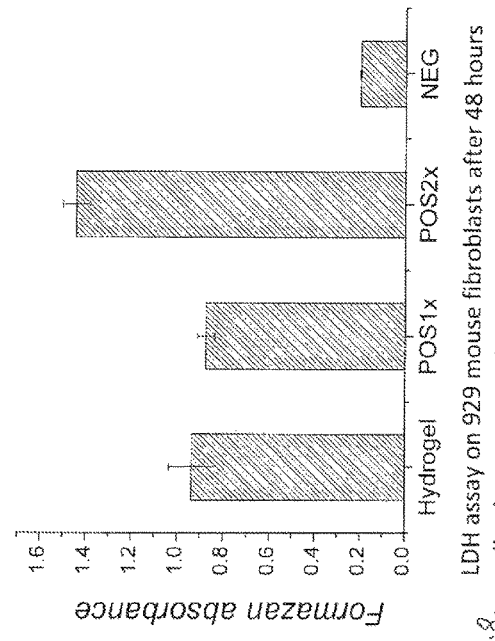
Fig. 7. Vital L929 mouse fibroblasts cultured on the hydrogel
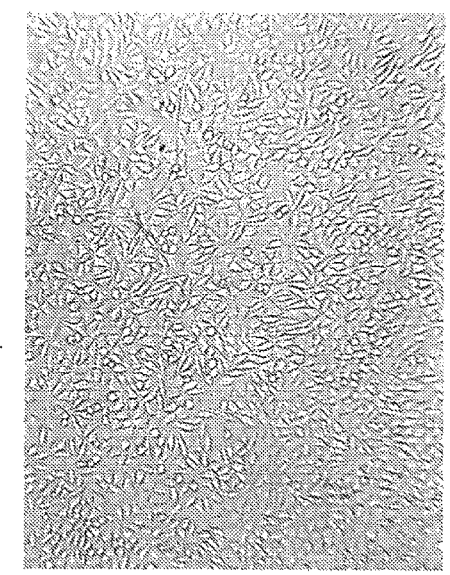
Fig. 8. LDH assay on 929 mouse fibroblasts after 48 hours cell culture on sample extract

COLLAGEN BASED MATERIALS

The present invention relates to collagen based materials, particularly though not exclusively to collagen based polymeric materials and to methods of manufacturing the same.

Biomaterials have been used in a wide range of pharmaceutical and medical applications such as, among others, tissue repair and regeneration, wound care, surgical haemostats, and haemorrhage control. A wide variety of products have been generated in different material forms such as film dressings, hydrocolloids, foam dressings, alginate dressings, hydrogels, non-adherent dressings, antimicrobial dressings, cleansing and debridement products, tissue engineering products and pharmacological products, which have been generated from either natural or synthetic sources.

Limitations with current products include, but are not limited to, induction of wound dehydration, hard eschar formation, and wound allergy. It is clear that a key challenge in the biomaterial industry is the design of versatile polymer systems which can be safely implanted in vivo allowing control of mechanical, physical and morphological properties.

Collagen is the main protein of the human body and provides tissues with unique structural organisation, mechanical properties and biological function. For this reason collagen-based biomaterials have been of great interest to the field. Collagen-based biomaterials can be processed into many forms including sponges, fibrous materials, scaffolds, and composite materials meaning applications are not limited. As a result, collagen-based biomaterials have been widely applied in the biomedical field in the fabrication of orthopaedic devices such as degenerative disc treatments, vascular devices such as heart valves and vascular grafts, and haemostat biomaterial. It has also been used in the context of wound treatment, for example in the fabrication of biomaterials where porous collagen-based materials are commonly used as scaffolds for tissue regeneration. The porous structure enables cellular growth, proliferation, migration and infiltration into a damaged site.

A key advantage of the porous structure of collagen-based biomaterials is that they allow the diffusion of nutrients through the structure enabling cells to grow and proliferate. However, although the pores are necessary to promote cellular proliferation during the tissue regeneration process, they render collagen-based biomaterial mechanically weak. For example, under physiological conditions collagen-based biomaterial instability has been observed in the form of shrinkage of the material. This ultimately results in non-controlled alteration of the biomaterial architecture and macroscopic geometry. Collagen scaffolds have traditionally been limited to being either porous but weak structures or dense but strong structures.

Covalent cross-linking of collagen fibrils and/or fibres is known in the art. Crosslinking generally increases the mechanical properties of a material. Examples of crosslinking reagents widely used include N-(3-dimethylaminopropyl)-N'-ethylcarbodiimide hydrochloride (EDC), glutaraldehyde (GTA), and hexamethylene diisocyanate (HDI). However problems with this approach include systematic variation of mechanical properties, cyto- and immune-incompatibility, and lack of preservation of protein structure. Furthermore, both GTA and HDI crosslinking may lead to the presence of unreacted functional groups, most likely aldehyde or amine groups in the collagen matrix.

Accordingly, the present invention aims to address at least one disadvantage associated with the prior art whether discussed herein or otherwise.

According to a first aspect of the present invention there is provided a collagen based polymeric material comprising collagen molecules and/or collagen derived molecules which have been functionalised by the addition of one or more ethylenically unsaturated moieties and which have been cross-linked via said moieties.

Suitably, the collagen based polymeric material comprises a hydrogel and/or biomaterial. Suitably, the collagen based polymeric material comprises a biomimetic material.

Suitably, the collagen based polymeric material comprises an irradiation cured material.

Suitably, the collagen based polymeric material comprises a photo cured material.

Suitably, the collagen based polymeric material comprises collagen and/or collagen derived molecules which have been functionalised by reaction with one or more ethylenically unsaturated molecules.

Suitably, the collagen based polymeric material comprises collagen molecules which have been functionalised by reaction with one or more vinyl molecules.

Suitably, the collagen based polymeric material comprises collagen and/or collagen derived molecules which have been functionalised by the addition of one or more ethylenically unsaturated moieties and which have been cross-linked via said ethylenically unsaturated moieties in an irradiation initiated polymerisation reaction.

Suitably, the collagen based polymeric material comprises collagen and/or collagen derived molecules which have been functionalised by the addition of one or more ethylenically unsaturated moieties and which have been cross-linked via said ethylenically unsaturated moieties in a photo polymerisation reaction.

Suitably, the collagen based polymeric material comprises collagen molecules which have been functionalised by the addition of one or more ethylenically unsaturated moieties and which have been cross-linked via said ethylenically unsaturated moieties.

Suitably, the collagen based polymeric material comprises collagen molecules and/or collagen derived molecules which have been functionalised by the addition of one or more moieties containing a vinyl group and which have been cross-linked via the vinyl groups.

Suitably, the collagen based polymeric material comprises collagen molecules which have been functionalised by the addition of one or more moieties containing a vinyl group and which have been cross-linked via the vinyl groups.

Suitably, the collagen based polymeric material comprises collagen which has been functionalised with vinyl bearing functional molecules. The collagen based polymeric material may comprise collagen which has been isolated from ECM of connective tissues and functionalised with vinyl bearing functional molecules.

Suitably, there is provided a collagen based polymeric material comprising collagen molecules which have been functionalised by the addition of one or more moieties containing vinyl groups and which have been cross-linked via said vinyl groups.

According to a second aspect of the present invention there is provided a method of producing a collagen based polymeric material wherein the method comprises cross linking functionalised collagen and/or collagen derived molecules having one or more ethylenically unsaturated moieties.

Suitably, the method comprises forming functionalised collagen and/or collagen derived molecules and then cross linking said functionalised collagen and/or collagen derived molecules. Alternatively, the method may comprise taking a composition comprising functionalised collagen and/or collagen derived molecules and then cross linking said functionalised collagen and/or collagen derived molecules.

Suitably, the method comprises the steps of:
(a) Functionalising collagen and/or collagen derived molecules by the addition of one or more ethylenically unsaturated moieties; and
(b) Cross linking of the functionalised collagen and/or collagen derived molecules of (a).

Suitably, there is provided a method of producing a collagen based polymeric material, the method being a two step process comprising the steps of:
(a) Functionalising collagen and/or collagen derived molecules by the addition of one or more ethylenically unsaturated moieties; and
(b) Cross linking of the functionalised collagen and/or collagen derived molecules of (a).

Suitably, the collagen based polymeric material comprises a hydrogel and/or biomaterial. Suitably, the collagen based polymeric material comprises a biomimetic material.

Suitably, the collagen based polymeric material comprises a material according to the first aspect. The method may comprise any feature as described in relation to the first aspect.

Suitably, the method comprises an irradiation curing step. Suitably, the method comprises crosslinking of the functionalised collagen and/or collagen derived molecules in step (b) in an irradiation initiated polymerisation reaction.

Suitably, the method comprises a photo curing step. Suitably, the method comprises crosslinking of the functionalised collagen and/or collagen derived molecules in step (b) in a photo polymerisation reaction.

Suitably, the method comprises functionalising collagen and/or collagen derived molecules by reaction with one or more ethylenically unsaturated molecules.

Suitably, the method comprises functionalising collagen by reaction with one or more vinyl molecules.

Suitably, the method comprises functionalising collagen molecules with one or more ethylenically unsaturated moieties and cross-linking said molecules via the unsaturated moieties;

Suitably, the method comprises functionalising collagen molecules and/or collagen derived molecules by the addition of one or more moieties comprising a vinyl group and cross-linking said molecules via the vinyl groups.

Suitably, the method comprises functionalising collagen molecules by the addition of one or more moieties containing a vinyl group and cross-linking said molecules via the vinyl groups.

Suitably, the method comprises functionalising collagen with vinyl bearing functional molecules. The method may comprise functionalising collagen which has been isolated from ECM of connective tissues with vinyl bearing functional molecules.

The method may use a composition according to the third aspect.

Suitably, there is provided a method of producing a collagen based polymeric material, the method being a two step process comprising the steps of:
(a) Functionalising collagen by the addition of one or more moieties comprising a vinyl group; and
(b) Crosslinking of the functionalised collagen and/or collagen derived molecules of (a).

According to a third aspect of the present invention there is provided a collagen based composition comprising a functionalised collagen and/or collagen derived molecule, wherein the collagen and/or collagen derived molecule is functionalised by addition of one or more an ethylenically unsaturated moieties.

Suitably, the composition comprises a functionalised collagen wherein the collagen and/or collagen derived molecule is functionalised by addition of one or more ethylenically unsaturated moieties.

Suitably, the composition comprises a functionalised collagen wherein the collagen and/or collagen derived molecule is functionalised by addition of one or more moieties comprising a vinyl group.

Suitably, the composition comprises a composition suitable for use in forming a material according to the first aspect. Suitably, the composition comprises a composition for use in a method according to the second aspect. Suitably, the composition comprises a composition for use in step (b) of a method according to the second aspect.

The composition may comprise any feature as described in relation to the first or second aspect.

The composition may be produced by a method according to step (a) of the method of the second aspect.

The material according to the first aspect of the present invention and/or the composition according to the second aspect of the present invention and/or the composition according to the third aspect of the present invention may comprise features as described hereafter.

Suitably, the material according to the first aspect of the present invention comprises functionalised collagen which has a preserved triple helical structure. Suitably, the material produced by the method of the second aspect of the present invention comprises functionalised collagen which has a preserved triple helical structure. Suitably, the composition according to the third aspect of the present invention comprises functionalised collagen which has a preserved triple helical structure.

As a non-limiting example, the quaternary structure of the functionalised collagen may be determined by analysis of the denaturation temperature of the protein. The denaturation temperature may be determined by any means known to a person skilled in the art. Suitably, the denaturation temperature is determined by circular dichroism spectroscopy.

The amount of triple-helically structured collagen may be determined by any suitable means. Suitably the amount of triple-helically structured collagen may be determined using circular dichroism spectroscopy. Unfunctionalised collagen displays a positive maximum absorption band at about 210 nm-230 nm relating to triple helix conformation. Unfunctionalised collagen also displays a negative minimum absorption band at about 190 nm relating to random coil conformation. Preferably the amount of triple-helically structured collagen may be measured as a ratio of the intensity of the absorption band for the material/composition containing functionalised collagen relative to that for to unfunctionalised collagen.

Alternatively, the triple helix conformation may be quantified via Attenuated total reflectance-Fourier transform infrared spectroscopy in non-soluble collagen hydrogels, for example by the method disclosed by B. B. Doyle, E. G. Bendit and E. R. Blout, *Biopolymers*, 1975, 14, 940-944. This method may utilize the fact that collagen displays distinct amide bands in ATR-FTIR spectrum: (i) amide A and B bands at 3300 and 3087 $cm^{-1}$, respectively, associated with the stretching vibrations of N—H groups; (ii) amide I and II bands, at 1650 and 1550 $cm^{-1}$, resulting from the stretching vibrations of peptide C=O groups as well as from N—H bending and C—N stretching vibrations, respectively;

(iii) amide III band centered at 1240 cm$^{-1}$, assigned to the C—N stretching and N—H bending vibrations from amide linkages, as well as wagging vibrations of CH$_2$ groups in the glycine backbone and proline side chains.

The amount of triple-helically structured collagen may be measured as a ratio of the intensity of the absorption band for the material/composition containing functionalised collagen relative to that for to unfunctionalised collagen wherein the ratio is determined by the negative minimum absorption peak at about 190 nm of a circular dichroism spectrum. Alternatively, or in addition the amount of triple-helically structured collagen may be measured as a ratio of the intensity of the absorption band for the material/composition containing functionalised collagen relative to that for to unfunctionalised collagen wherein the ratio is determined by the positive maximum absorption peak at about 210 nm-230 nm, more preferably at about 221 nm, of a circular dichroism spectrum.

In preferred embodiments the ratio of the intensity of the absorption band for the material/composition containing functionalised collagen relative to that for unfunctionalised collagen may be up to 1:1.

In preferred embodiments the ratio of the intensity of the absorption band for the material/composition containing functionalised collagen relative to that for unfunctionalised collagen may be at least 0.5:1.

Alternatively, the degree of triple helix preservation in resulting materials may be quantified via determination of FTIR absorption ratio between amide III and 1450 cm$^{-1}$ bands ($A_{III}/A_{1450}$). This quantity should be equal to one in the case of completely preserved triple helix structure (L. He, C. Mu, J. Shi, Q. Zhang, B. Shi and W. Lin, *Int. J. Biol. Macromol.*, 2011, 48, 354-359).

The collagen may be of any type, including but not limited to, types I, II, III, and IV or any combination thereof. In a preferred embodiment the collagen is type I collagen. The collagen may be atelopeptide or telopeptide-containing collagen. Alternatively the collagen may be type II collagen. Alternatively the collagen may be type III collagen. Alternatively the collagen may be type IV collagen. Alternatively the collagen may be any combination of types I, II, III, and IV collagen.

The collagen may be obtained from any suitable source. Collagen may be extracted and purified from any suitable source. The collagen may be obtained from a biological source. For example, collagen may be extracted and purified from a human, mammalian, or avian source. Examples of convenient mammalian and avian sources are, but are not limited to chicken, bovine, porcine, ovine, murine, lupine or equine. Suitable sources of collagen include, but are not limited to, skin, tendons, bone, cartilage, ligaments, fascia, intestinal submucosa, and placenta. The collagen may be isolated from ECM of connective tissues. The collagen may be extracted and purified from rat tails. Suitable methods of extraction of collagen will be well known to a person skilled in the art. Alternatively, collagen may be recombinantly produced. Methods of recombinant collagen production will be well known to a person skilled in the art. Collagen may be artificially synthesised.

The ethylenically unsaturated moieties can be any suitable moeities. By ethylenically unsaturated monomer we mean to refer to any monomer including any one or more unsaturated C—C bond(s) in a compound such as those found in alkenes, alkynes, conjugated and unconjugated dienes, functional alkenes etc. The ethylenically unsaturated monomer may be flexible or rigid. The ethylenically unsaturated monomer may be hydrophilic or hydrophobic. Preferably the ethylenically unsaturated monomer is glycidyl methacrylate (GMA), 4-vinylbenzyl chloride (4VBC), or methacrylic anhydride (MA). Alternatively the ethylenically unsaturated monomer may be glycidyl methacrylate (GMA). Alternatively the ethylenically unsaturated monomer may be 4-vinylbenzyl chloride (4VBC). Alternatively the ethylenically unsaturated monomer may be methacrylic anhydride (MA). In one preferred embodiment glycidyl methacrylate is used as a flexible, hydrophilic monomer. In another preferred embodiment 4-vinylbenzene chloride is used as a rigid, hydrophobic monomer. In a preferred embodiment the ethylenically unsaturated monomer is glycidyl methacrylate or 4-vinylbenzyl chloride or methacrylic anhydride. The selection of the ethylenically unsaturated monomer may be based on the material properties required in the product. 4-VBC-based systems may be stiffer and take up more water, GMA-based systems may be more elastic but swell less. MA-based systems may show intermediate properties between 4-VBC-based systems and MA-based systems.

The ethylenically unsaturated monomer may be coupled to the collagen by any suitable method. The ethylenically unstaurated monomer may be coupled to the collagen by any suitable reaction. Suitably the ethylenically unsaturated monomer is coupled to the collagen via an electrophilic substitution reaction. Any suitable electrophile may be used. Exemplary electrophiles include, but are not limited to, activated esters, activated amides, Michael acceptors, alkyl halides, aryl halides, acyl halides, and isothiocyanates. In one preferred embodiment the electrophile is an alkyl halide. In another preferred embodiment the electrophile is an epoxy group. In another preferred embodiment the electrophile is an ester group.

Functional groups which may be involved in the reaction include the ε-amino functions of lysine and hydroxylysine, hydroxyl functions of serine, threonine and tyrosine, and thiol groups of cysteine. Preferably the functionalisation is chemo-selective. In a preferred embodiment the functionalisation is predominantly on the lysine side chains of the collagen. ε-amino functions of lysine are known to be highly reactive species and will therefore be the predominant reaction. The functionalisation may occur via amine groups. Preferably the functionalisation may occur by the amine group of lysine side chains.

Suitably, the material according to the first aspect comprises collagen molecules which have been reacted at one or more lysine groups thereof to combine them with one or more ethylenically unsaturated monomers and which monomers have then been reacted to cross link collagen molecules and form the collagen based polymeric material.

Suitably, the method according to the second aspect comprises reacting collagen molecules at one or more lysine groups thereof to combine it with one or more ethylenically unsaturated monomers and then reacting said monomers to cross link collagen molecules and to form the collagen based polymeric material.

Suitably, the composition according to the third aspect comprises collagen molecules which have been reacted at one or more lysine groups thereof to combine them with one or more ethylenically unsaturated monomers.

The degree of collagen functionalisation may be controlled so as to influence the properties of the final composition. The degree of functionalisation may be between 15 mol % and 90 mol %, more preferably between 5 mol % and 100 mol %, suitably, between 20 and 95 mol %, most preferably between 30 and 90 mol %. The degree of functionalisation may be selected depending on the required properties of the hydrogel.

The collagen functionalisation reaction may be carried out in any suitable medium. Preferably the collagen functionalisation reaction is carried out in an aqueous medium. Preferably the collagen functionalisation reaction is carried out in an acidic solution. The collagen functionalisation reaction may be carried out in a medium comprising hydrochloric acid (HCl). More preferably the collagen functionalisation reaction may be carried out in an aqueous medium comprising hydrochloric acid (HCl).

The collagen functionalisation reaction may be carried out in a medium containing any suitable concentration of acid. Preferably the collagen functionalisation reaction is carried out in a medium containing up to 50 mM acid, suitably up to 40 mM, more suitably up to 30 mM, preferably up to 20 mM, most preferably up to 10 mM acid.

In the collagen functionalisation reaction the collagen may be present at any suitable concentration. In the collagen functionalisation reaction the collagen is preferably present at a concentration of between about 0.2 wt % and 1.0 wt %, more preferably between about 0.25 wt % and 0.5 wt %, most preferably about 0.25 wt %.

The collagen functionalisation reaction may be carried out at any suitable temperature. In one preferred embodiment the collagen functionalisation reaction is carried out at about 10-25° C. Most preferably, the collagen functionalisation reaction is carried out at about 25° C.

The collagen may be stirred in the reaction medium for any suitable period of time. Preferably the collagen may be stirred in the reaction medium until a clear solution is obtained. Suitably this may be up to 12 hours, more suitably up to 16 hours, most suitably up to 24 hours. Preferably the collagen is fully solubilised in the reaction medium.

The reaction mixture containing collagen may be neutralised prior to addition of the ethylenically unsaturated monomer. The reaction mixture may be neutralised by any suitable method. The reaction mixture may be neutralised via the addition of an alkali. Preferably the reaction mixture is neutralised via the addition of NaOH. Preferably the reaction mixture is neutralised to a pH between 7.2 and 7.5, more preferably to a pH of 7.4.

A surfactant may be added to the reaction mixture. A surfactant may be added to increase the miscibility of the ethylenically unsaturated monomer. By surfactant we mean to refer to any compound that increases the miscibility of the ethylenically unsaturated monomer in solution, especially in aqueous solution. The surfactant may be any suitable surfactant. Preferably the surfactant is a non-toxic surfactant. In a most preferred embodiment the surfactant is a polymeric compound, such as a polysorbate or a poly(ethylene oxide)-poly(propylene oxide)poly(ethylene oxide) triblock (PEO-PPO-PEO) copolymer. Most preferably the surfactant is polysorbate-20, $PEO_{40}$-$PPO_{20}$-$PEO_{-40}$, or any combination thereof. The surfactant may be selected from the Tween® or Pluronic® family. The surfactant may be present at any suitable concentration. Preferably the surfactant is present at a concentration of between 0.1 wt % and 2.0 wt %, preferably at a concentration of between 0.5 wt % and 1.5 wt %, most preferably at a concentration of 1.0 wt %. It will be known to a person skilled in the art that the concentration of surfactant may vary depending on the type of surfactant used.

The ethylenically unsaturated monomer may be added to the reaction mixture at any suitable molar ratio of monomer to lysine. The molar ratio may be between 5:1 and 150:1. More preferably the molar ratio is any one of 10:1, 25:1, 50:1, and 75:1. Most preferably the molar ratio is between 25:1 and 75:1. The molar ratio of monomer to lysine may for example be between 25:1 and 50:1. It will be appreciated by a person skilled in the art that the molar ratio may be varied to achieve varying mechanical properties of the material.

A catalyst may also be added to the reaction mixture. The catalyst may be any suitable catalyst. Preferably the catalyst is triethylamine (TEA). The molar ratio of catalyst to ethylenically unsaturated monomer is preferably between 1:5 and 2:1, more preferably between 1:2 and 1.5:1, most preferably 1:1. If no catalyst is added to the reaction the degree of functionalisation may be minimal.

The collagen functionalisation reaction may proceed for any suitable period of time. Preferably the functionalisation reaction is allowed to proceed for up to 24 hours. Preferably the functionalisation reaction is allowed to proceed for at least 8 hours. Most preferably, the functionalization reaction may proceed for up to between 8 and 24 hours.

The collagen functionalisation reaction may be stopped by any suitable means. The reaction may be stopped by dialysis. However, in a preferred embodiment the collagen functionalisation reaction is stopped by combination with reaction stopping means, suitably by combination with a coagulation agent, suitably by combination with a coagulation liquid. The collagen functionalisation reaction is suitably stopped by the addition of a coagulation liquid. The coagulation liquid may be any suitable coagulation liquid for collagen. The coagulation liquid may be any suitable organic solvent, e.g. acetone, ethanol, methanol. In a preferred embodiment the coagulation liquid is ethanol. By stopping the functionalisation reaction the functionalised collagen is precipitated from solution. Precipitation may be carried out in any suitable volume of coagulation liquid. Preferably the volume excess of the coagulation liquid is between 5- and 15-fold, more preferably 10-fold. In a preferred embodiment the precipitation of functionalised collagen is allowed to proceed for at least about 12 hours, more preferably at least about 16 hours, most preferably at least about 24 hours. The addition of a coagulation liquid may be found to increase the reaction yield and/or enhance purification and/or may be quicker when compared to the conventional method of dialysis.

The precipitated functionalised collagen may be harvested by any suitable means. Preferably the precipitated functionalised collagen is harvested by centrifugation. Preferably centrifugation is carried out at up to 20,000 rpm, more suitably up to 10,000 rpm. Centrifugation may be carried out at any suitable temperature for any suitable period of time. In a preferred embodiment centrifugation is carried out at a temperature of between about 4° C. and 20° C. for up to 60 minutes. It will be appreciated by those skilled in the art that the speed and length of time of centrifugation may vary depending on the specifications of the equipment used.

Functionalised collagen may be crosslinked in any aqueous solution. More preferably functionalised collagen may be crosslinked in a buffered aqueous solution. Alternatively, functionalised collagen may be crosslinked in diluted hydrochloric acid solution. Preferably the solution is phosphate buffered saline (PBS) or 10 mM HCl solution. By PBS is meant a water-based salt solution containing sodium chloride, sodium phosphate, and, in some formulations, potassium chloride and potassium phosphate. A suitable PBS composition may be 0.01 M phosphate buffered saline (NaCl 0.138 M; KCl—0.0027 M. PBS solutions may be prepared by any method known to a person skilled in the art, for example but not limited to using PBS buffer tablets. The concentration of the buffer may be suitably selected to maintain a desired pH. The pH is preferably from 7 to 8, more preferably from 7.2 to 7.6, most preferably 7.4.

The crosslinking reaction mixture may comprise any suitable concentration of functionalised collagen. The crosslinking reaction mixture preferably comprises between 0.5 and 1.5 wt % of functionalised collagen, more preferably 0.7 to 1.0 wt %, most preferably 0.7 wt %.

A photoinitiator may be added to the crosslinking reaction mixture. By photoinitiator we mean to refer to any compound which, on absorption of light, generates a reactive species (which may be, for example, an ion or radical) and initiates a polymerisation reaction. The photoinitiator may be any suitable photoinitiator. The photoinitiator may be a cationic photoinitiator or a radical photoinitiator. Preferably the photoinitiator is a radical photoinitiator. The radical photoinitiator may be a type 1 or type 11 photoinitiator. Preferably the photoinitiator is water-compatible. By water-compatible we mean to refer to compounds whose reactivity is not inhibited by water. Preferably the photoinitiator is a cyto-compatible photoinitiator. Most preferably the photoinitiator is Irgacure® 2959 [4-(2-hydroxyethoxy)phenyl-(2-hydroxy-2-propyl)ketone] (I2959).

The crosslinking reaction mixture preferably comprises between about 0.2 wt % and 2.0 wt % photoinitiator, more preferably between 0.5 wt % and 1.5 wt %, most preferably 1.0 wt %. It will be appreciated to a person skilled in the art that the amount of photoinitiator may vary depending on the photoinitiator used.

A crosslinking reaction mixture may be prepared via stirring of functionalized collagen in previously-mentioned aqueous solution at 4° C. until a clear solution is formed. More preferably, a solution is formed after at least 24 hours stirring, most preferably between 24 and 60 hours stirring.

The cross linking reaction is suitably carried out in the dark. By in the dark we mean to refer to the absence of UV or visible light.

The UV irradiation stage may be carried out in any suitable receptacle. Suitably the receptacle is optically clear. Suitably for small-scale applications the receptacle may be a Petri dish.

In certain embodiments air bubbles may be removed from the functionalised collagen solution following the stirring stage. Air bubbles may be removed by any method known in the art. In a preferred embodiment the air bubbles are removed by incubation in a vacuum desiccator.

Suitably, the functionalised collagen is crosslinked by UV light irradiation. It is known by a person skilled in the art that the wavelength used for the UV light irradiation may depend upon the photoinitiator used. Any photoinitiator with aborbance in the range of 200-400 nm may be applied. In a preferred embodiment functionalised collagen may be irradiated with UV light at a wavelength of 365 nm in the presence of Irgacure® 2959. The UV irradiation may proceed for about 10 to 60 minutes, more preferably about 20 to 30 minutes. The irradiation may proceed for at least 20 minutes for each side of a sample, most preferably for 30 minutes for each sample side.

The formed collagen based polymeric material, may be washed. The formed collagen based polymeric material may be washed via any suitable method. Preferably, the formed collagen based polymeric material is washed with distilled water and/or PBS solution. In a preferred embodiment the formed collagen based polymeric material is washed for up to at least 24 hours, more preferably up to at least 48 hours, most preferably up to at least 72 hours.

The material according to the first aspect of the present invention may be stable in any solution. Preferably the material according to the first aspect of the present invention is stable in water. Preferably the material according to the first aspect of the present invention is stable in aqueous solution.

Suitably the material according to the first aspect of the present invention has increased mechanical stability and reduced water uptake when compared to non-functionalised collagen.

A composition according to the first aspect may have suitable mechanical stability as measured by any suitable means. Suitable methods for measuring the mechanical stability of the material will be well known to a person skilled in the art. Preferably the mechanical stability of collagen based polymeric material is measured by the compressive modulus (E). Suitably the compressive modulus is measured in Pa, more preferably kPa. Preferably the compressive modulus is between 0.01 kPa and 300 kPa, preferably between 50 kPa and 300 kPa, more preferably between 100 kPa and 300 kPa, more preferably 200 kPa to 300 kPa, most preferably between 250 kPa and 300 kPa. In a most preferred embodiment the compressive modulus is at least about 100 kPa.

A composition according to the first aspect may have a suitable swelling ratio as measured by any suitable means. Suitable methods for measuring the swelling ratio of the material will be well known to a person skilled in the art. The swelling ratio may be between 100 wt % and 3000 wt %. Preferably the swelling ratio is higher than at least 100 wt %, preferably higher than at least 500 wt %, more preferably higher than at least 1000 wt %, most preferably higher than at least 2000 wt %. In a most preferred embodiment the swelling ratio is at least about 2500 wt %.

Suitably, the composition according to the first aspect of the present invention is biocompatible. In certain embodiments, vital cells may be observed after direct and indirect culture and following material degradation.

A composition according to the first aspect may have a suitable degradation time and the degradation time of the material may be measured by any suitable means. Suitable methods for measuring the degradation time of the material will be well known to a person skilled in the art. The degradation time of the material may be between about 3 and 90 days. The composition may comprise a filler phase, suitably a ceramic filler phase. Addition of a ceramic filler phase in the material may ensure a degradation time higher than 30 days. Preferably the degradation time is higher than at least 3 days, preferably higher than at least 10 days, preferably higher than at least 20 days, preferably higher than at least 30 days, more preferably higher than at least 40 days, most preferably higher than at least 50 days. In a most preferred embodiment the degradation time is at least about 60 days.

A composition according to the first aspect may have a suitable denaturation temperature ($T_d$) and the denaturation temperature of the material may be measured by any suitable means. Suitable methods for measuring the denaturation temperature of the material will be well known to a person skilled in the art. The denaturation temperature may be between about 60 and 90° C. Preferably the denaturation temperature is at least about 60° C., more preferably at least 70° C., most preferably at least 80° C. In a most preferred embodiment the denaturation temperature is at least about 90° C.

Suitably, a method according to the second aspect of the present invention may provide greater control over the degree of functionalisation in step (a) so that material geometry and internal architecture can be controlled and tuned in step (b).

Functionalised collagen materials may be in the form of cast films, fibres, filaments or scaffolds. For the manufacture of fibres, which have a discrete length, or filaments, which have a continuous length, suitable methods may include wet spinning, electrospinning, or combinations thereof wherein the fibre or filament is formed by phase separation following extrusion of the functionalised collagen.

According to a fourth aspect of the present invention there is provided a method of producing a collagen based polymeric material in the form of one or more fibres and/or one or more filaments and/or one or more films wherein the method comprises cross linking functionalised collagen and/or collagen derived molecules having one or more ethylenically unsaturated moieties.

Suitably, the method comprises functionalising collagen and/or collagen derived molecules by the addition of one or more ethylenically unsaturated moieties;

Suitably the method comprises combining the functionalised collagen and/or collagen derived molecules with a vehicle.

Suitably, the method comprises wet spinning the functionalised collagen and/or collagen derived molecules.

Suitably, there is provided a method of producing a collagen based polymeric material in the form of one or more fibres and/or one or more filaments and/or one or more films wherein the method comprises the steps of:
  (a) Functionalising collagen and/or collagen derived molecules with one or more ethylenically unsaturated moieties;
  (b) Combining the functionalised collagen and/or collagen derived molecules with a vehicle; and
  (c) Wet spinning the functionalised collagen and/or collagen derived molecules;

Suitably, the method comprises a method of forming fibres.

Suitably, the method comprises a method of forming filaments.

The method may comprise a method of forming films.

Suitably, the method comprises a method according to the second aspect. The method may comprise an feature as described in relation to the second aspect.

The method may comprise manufacturing a material according to the first aspect.

The method may use a composition according to the third aspect.

It may be more straightforward to adjust experimental parameters using wet spinning techniques to form the fibres and/or filaments and/or films. In this way fibre diameter and/or length can be easily varied. It will be appreciated by a person skilled in the art that variability of fibre diameter and/or size will be necessary depending on the targeted application.

Preferred components for step (a) of the fourth aspect and the amounts present are as defined in relation to the first, second and third aspects of the present invention.

Steps (b) and (c) of the fourth aspect may be carried out with a functionalised collagen composition according to the third aspect of the present invention.

Steps (b) and (c) may be carried out with any suitable concentration of functionalised collagen. Preferably the concentration of functionalised collagen is between about 5 wt % and 16 wt %, more preferably between about 5 wt % and 10 wt %, most preferably 8 wt %.

By vehicle in step (b) we mean to refer to any medium in which functionalised collagen is solubilised. In the prior art solubilisation of collagen based components has been achieved by using toxic solvents such as 1,1,1,3,3,3-hexafluoro-2-propanol (HFIP). However, the use of toxic solvents may render cast films, fibres, filaments or scaffolds cytotoxic and may limit their applications. Suitably the functionalised collagen according to the present invention has a conserved triple helical structure. Suitably the functionalised collagen according to the present invention may be more amenable to solubilisation in non-toxic vehicles. Suitably the functionalised collagen according to the present invention may be more amenable to solubilisation in cyto-compatible vehicles. More suitably the functionalised collagen according to the present invention may be more amenable to solubilization in aqueous or organic vehicles or combination thereof.

The vehicle of step (b) may be any suitable medium. The medium may comprise, for example but not limited to, ethanol and PBS. PBS solutions may be prepared by any method known to a person skilled in the art, for example using PBS buffer tablets. In preferred embodiments the PBS buffer has a higher salt concentration that standard PBS buffer. Preferably the salt concentration is 1-20 fold higher that standard PBS buffer, more preferably 1-10 fold, most preferably 5-fold higher. Preferably the volume ratio of ethanol to PBS is between 1:1 and 1:5, more preferably between 1:1 and 1:2, most preferably 1:1. In a further preferred embodiment the vehicle is PBS buffer only.

The solution containing the vehicle and functionalised collagen may be stirred for any suitable period of time. The solution may be stirred for between about 24 and 72 hours. Preferably the solution is stirred for at least up to about 24 hours, more preferably at least up to about 48 hours. Preferably the solution is stirred for less than at least 72 hours, more preferably less than about 60 hours, most preferably less than about 50 hours. In a preferred embodiment the solution is stirred for about 48 hours.

The solution may be stirred at about any suitable temperature, most suitably about 25° C.

The wet spinning of step (c) may be carried out by any method known to a person skilled in the art. Electrospinning, force-spinning or centrifugal spinning may be used wherein the extruded polymer jets are directed in to a suitable coagulating system. The functionalised collagen containing solution may be loaded into any wet spinning extrusion system known in the art. As a non-limiting example, the functionalised collagen containing solution is loaded into a syringe. In another embodiment the functionalised collagen containing solution is loaded into an industrially-applicable system. As a further non-limiting example, the functionalised collagen containing solution is loaded in to a tank. It is then pumped in to a spinneret that is submerged in a spin bath containing a coagulating system. Continuous filaments are then formed as the extruded polymer jets emerge from the spinneret. The filaments may then be optionally stretched before then drying and winding on to a suitable package. The filaments may also be chopped to make staple fibres at the end of this process.

The functionalised collagen containing solution may be wet spun against any suitable coagulating system. By suitable system we mean to refer to any system, solvent and/or nonsolvent system and any combination thereof that causes the phase separation of the functionalised collagen upon contact. Preferably the solution is non-cytotoxic. In preferred embodiments the solution is an ethanol solution, acetone solution, methanol solution and any combination thereof A photoinitiator may be added during or after any of steps (b) and/or (c). By photoinitiator we mean to refer to any compound which, on absorption of light, generates a reactive species (which may be, for example, an ion or radical) and initiates a polymerisation reaction. The photoinitiator may be any suitable photoinitiator. The photoinitiator may be a cationic photoinitiator or a radical photoinitiator. Preferably the photoinitiator is a radical photoinitiator. The radical photoinitiator may be a type 1 or type 11 photoinitiator. Preferably the photoinitiator is water-compatible. By water-compatible we mean to refer to compounds whose reactivity is not inhibited by water. Preferably the photoinitiator is a cyto-compatible photoinitiator. Most preferably the photoinitiator is Irgacure® 2959 [4-(2-hydroxyethoxy) phenyl-(2-hydroxy-2-propyl)ketone] (12959).

Photoinitiation may be carried out during or after any of steps (b) and (c) or during or after fibre formation. Alternatively, photoinitiation can be carried out simultaneously with fibre formation. Alternatively fibre formation can be obtained simultaneously to introduce covalent crosslinking.

In certain embodiments a photoinitiator is added before and/or during step (b).

In a most preferred embodiment a photoinitiator is added to the solution against which the functionalised collagen is spun in step (c).

Although the photoinitiator may be added at any step of the process according to the fourth aspect of the present invention, it may be advantageous to add the photoinitiator to the solution against which the functionalised collagen is spun in step (c). This is because the photoinitiator may interfere with the spinning stability if added before step (c).

The solid fibres and/or filaments may be collected in any suitable form. The solid fibres and/or filaments may be collected in the form of webs, tows, yarns, or may be coated directly onto three-dimensional objects such as pre-formed implants. The solid fibres and/or filaments may be collected in the form of nonwovens.

The functionalised collagen fibres and/or filaments and/or films according to the fourth aspect of the present invention may be of any suitable diameter. The diameter may be between about 0.01 µm and 50 µm. It will be appreciate by a person skilled in the art that the diameter of the functionalised collagen fibres and/or filaments and/or films may be varied depending on the application.

The functionalised collagen fibres and/or filaments and/or films according to the fourth aspect of the present invention may be of any suitable pore size. The pore size may be between about 5 µm and 350 µm. It will be appreciated by a person skilled in the art that the pore size of the functionalised collagen fibres and/or filaments and/or films may be varied depending on the application. Webs, tows, yarns and/or nonwovens of functionalised collagen fibres and/or filaments and/or films according to the fourth aspect of the present invention may be of any suitable pore size. The pore size may be between about 5 µm and 350 µm. It will be appreciated by a person skilled in the art that the pore size of the webs, tows, yarns and/or nonwovens of functionalised collagen fibres and/or filaments and/or films may be varied depending on the application.

The compositions and processes of the present invention may have applications in tissue repair and regeneration, for example as scaffolds for periodontal ligament repair, cancellous bone repair in maxillofacial application, around implants, periodontal defects, and bifurcation defects among many others. The compositions and processes of the present invention may have applications in wound treatment and management, for example as wound dressings and fibrous patches among many others.

According to a fifth aspect of the present invention there is provided a provided a collagen based polymeric material comprising collagen and/or collagen derived moieties cross linked to one another via moieties added at lysine terminations of the collagen and/or collagen derived moieties.

Suitably, the polymeric material, displays full biocompatibility. Suitably, the polymeric material displays high water uptake, suitably >1000 wt. %. Suitably, the polymeric material displays high compression modulus, suitably >100 kPa.

Suitably, there is provided a provided a collagen based polymeric material comprising collagen moieties cross linked to one another via moieties added at lysine terminations of the collagen molecules.

Suitably, the composition comprises a composition according to the first aspect. The composition may comprise any feature as described in relation to the first, second, third and/or fourth aspect.

The present invention will now be further described by way of example with reference to the accompanying figures in which:

FIG. 5 shows a L929 cell morphology picture following culture on exemplarily GMA-based hydrogel extract;

FIG. 6 shows a L929 cell morphology picture following culture on cell culture medium;

FIG. 7 shows a L929 cell morphology picture of vital cells cultured in contact with the exemplarily GMA-based hydrogel after 24 hours; and FIG. 8 shows an LDH assay of cells cultured on sample extracts of GMA-based hydrogel.

EXAMPLES

Isolation of Type I Collagen

Figure 1:
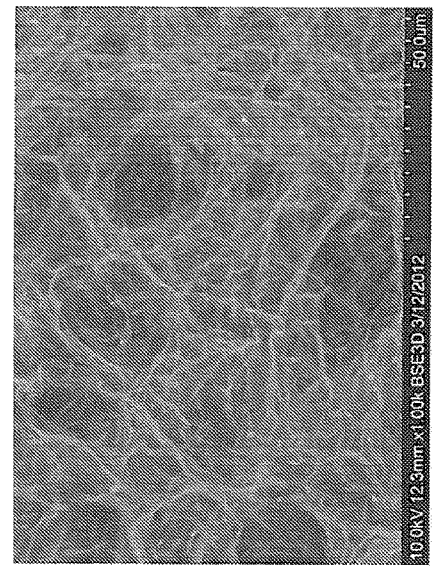
FIG. 1 shows compression modulus of collagen hydrogels.

Type I collagen was isolated from rat tail tendons. Frozen rat tails were thawed in ethanol for 20 minutes. Individual tendons were pulled from the tendon sheath, minced, and placed in 17.4 M acetic acid solution at 4° C. for 72 hours. After 72 hours, the mixture was centrifuged at 20,000 rpm for 1 hour. The pellet was discarded and the crude collagen solution was neutralised with 0.1 M NaOH. The solution was stirred overnight (16-24 hours) at 4° C. before a further centrifugation step at 10,000 rpm for 45 minutes at 4° C. The supernatant was removed and an equal volume of 17.4 M acetic acid was added to re-solubilise the collagen pellet. The mixture was freeze-dried to obtain the collagen.

Example 1

Synthesis of Glycidyl Methacrylate (GMA)-Functionalised Collagen (Collagen Based Composition)

0.25 wt % of the isolated type I collagen was stirred in 10 mM HCl solution at 25° C. for 4 hours until a clear solution was obtained. The solution was neutralised to pH 7.4 with NaOH]. Glycidyl methacrylate (GMA) was added in a 10, 25, 50, or 75 molar excess with respect to the collagen lysines along with an equimolar monomer amount of triethylamine (TEA). 1.0 wt % Tween®-20 was added to increase monomer miscibility. The reaction was allowed to proceed for 24 hours at 25° C. After 24 hours, the mixture was precipitated in a 10-15 volume excess of ethanol and stirred for 48 hours at 25° C. Ethanol-precipitated functionalised collagen was recovered by centrifugation at 10,000 rpm for 60 minutes at 4° C. The pellet was air dried.

Preparation of Photo-Crosslinked Glycidyl Methacrylate (GMA)-Functionalised Collagen Hydrogel (Collagen Based Polymeric Material)

GMA-functionalised collagen was stirred in PBS solution containing 1 wt % Irgacure® 2959 [4-(2-hydroxyethoxy) phenyl-(2-hydroxy-2-propyl)ketone] (I2959) at 4° C. for 48 hours. The PBS-Irgacure® solution was prepared by stirring at 50° C. in the dark until a clear solution was obtained. The resulting solution was then poured into a Petri dish and incubated in a vacuum dessicator (25° C., up to 20 minutes) to remove air bubbles. Crosslinking was achieved by UV irradiation using a Spectroline UV lamp] at 365 nm and an intensity of 9 mW/cm² for 20 minutes on each side of the Petri dish. The formed hydrogel was washed in distilled water and PBS to remove unreacted compounds for at least 48 hours.

Example 2

Synthesis of 4-Vinylbenzyl Chloride (4VBC)-Functionalised Collagen (Collagen Based Composition)

4-vinylbenzyl chloride (4VBC)-functionalised collagen was prepared by the same method outlined for example 1.

Preparation of Photo-Crosslinked 4-Vinylbenzyl Chloride (4VBC)-Functionalised Collagen Hydrogel (Collagen Based Polymeric Material)

4VBC-functionalised collagen was stirred in 10 mM HCl solution containing 1 wt % Irgacure® 2959 [4-(2-hydroxyethoxy)phenyl-(2-hydroxy-2-propyl)ketone] (I2959) at 4° C. for 48 hours. The resulting solution was then poured into a Petri dish and incubated in a vacuum desiccator (25° C., up to 20 minutes) to remove air bubbles. Crosslinking was achieved by UV irradiation using a Spectroline UV lamp at 365 nm and an intensity of 9 mW/cm² for 20 minutes on each side of the Petri dish. The formed hydrogel was washed in distilled water and PBS to remove unreacted compounds for at least 48 hours.

Example 3

Synthesis of Methacrylic Anhydride (MA)-Functionalised Collagen

Methacrylic anhydride (MA)-functionalised collagen was prepared by the same method outlined in Example 1.

Preparation of Photo-Crosslinked Methacrylic Anhydride (MA)-Functionalised Collagen Hydrogel (Collagen Based Polymeric Material)

The photo-crosslinked methacrylic anhydride (MA)-functionalised collagen hydrogel was prepared by the same method outlined in Example 1.

Hydrogel Testing

Resulting hydrogels were tested as for swelling behaviour and mechanical properties together with a commercially-available wound dressing product, Aquacel®.

Aquacel® is a sodium carboxymethylcellulose-based wound dressing manufactured by Convatec. It is produced as a textile fibre and is available both as a 'ribbon' for packing cavities, and as a flat non-woven pad for application to larger open wounds.

Chemical Characterisation of Hydrogels

Degree of functionalisation (F) of collagen lysines was determined by 2,4,6-trinitrobenzenesulfonic acid (TNBS) colorimetric assay. 11 mg of the dry sample was mixed with 1 mL of 4 wt % $NaHCO_3$ pH 8.5 and 1 mL of 0.5 wt % TNBS solution at 40° C. under mild shaking. After 4 hours, 3 mL of 6 M HCl solution was added and the mixture was heated to 60° C. Samples were cooled and extracted 3 times with anhydrous ethyl ether to remove any unreacted TNBS. A reference sample was prepared in the same way except that the HCl solution was added before the addition of TNBS. The content of free amino groups and F were calculated as follows:

$$\frac{moles(Lys)}{g(collagen)} = \frac{2 \times Abs(346\ nm) \times 0.02}{1.4 \times 10^4 \times b \times x}$$

$$\text{and } F = 1 - \frac{moles(Lys)_{Funct \cdot Collagen}}{moles(Lys)_{Collagen}}$$

wherein Abs(346 nm) is the absorbance value at 346 nm, $1.4 \times 10^4$ is the molar absorption coefficient for 2,4,6-trinitrophenyl lysine in L/mol cm$^{-1}$, b is the cell path length (1 cm), x is the sample weight in grams, and moles $((Lys)_{Funct \cdot Collagen}$ and moles$((Lys)_{Collagen}$ represent the lysine molar content of functionalised and native collagen respectively.

Collagen functionalisation was also investigated by $^1$H-NMR. 10 mg of dry sample was dissolved in 1 mL deuterium oxide and the $^1$H-NMR spectra was recorded on a Bruker Avance spectrophotometer (55 MHz).

Raman spectra were also obtained to investigate the collagen functionalisation. A Renishaw microscope with 2 exciting lasers (HeNe at 663 nm, IR diode laser at 780 nm) was used to obtain Raman spectra of dry samples (up to 100 mg).

Attenuated Total Reflectance Fourier-Transform Infrared (ATR FT-IR) was also carried out on dry samples (up to 100 mg) using a Perkin-Elmer Spectrum BX spotlight spectrophotometer with diamond ATR attachment. Scans were conducted from 4000 to 600 cm$^{-1}$ with 64 repetitions averaged for each spectrum. Resolution was 4 cm$^{-1}$ and interval scanning was 2 cm$^{-1}$.

Collagen Conformation

The conformation of crosslinked collagen was investigated using circular dichroism (CD). CD spectra were obtained with a Jasco J-715 spectropolarimeter. Samples had a concentration of 0.2 mg/mL in 10 mM HCl. CD spectra were acquired with a 2 nm band width and 20 nm/min scanning speed. Solutions were measured in a quartz cell with a pathlength of 1.0 mm. Temperature ramp measurements at a fixed wavelength of 221 nm were conducted between 20 and 60° C. with a 20° C./hour heating rate. The denaturation temperature ($T_d$) was determined as the midpoint of thermal-transition.

Protein conformation of photo-crosslinked collagen networks was investigated by Wide Angle X-ray Scattering (WAXS). WAXS measurements were carried out on dry samples with a Bruker D8 Discover (40 kV, 30 mA, 0.154 nm, X-ray wavelength A=0.154 nm). The detector was set at a distance of 15 cm covering 2θ from 5 to 40°. The collimator was 2.0 mm and the exposure time was 50 s per frame. WAXS measurements were coupled with Differential Scanning calorimetry (DSC) in order to investigate the thermal denaturation of collagen samples (TA Instruments Thermal Analysis 2000 System and 910 Differential Scanning calorimeter cell base). DSC temperature scans were conducted over a 10 to 200° C. temperature range at a 10° C./min heating rate. 10-15 mg samples were used for each measurement. The DSC cell was calibrated using indium with 20° C./min heating rate under 50 cm³/min nitrogen atmosphere.

Scanning Electron Microscopy

Sample morphological investigations were carried out via SEM and EDS (JEOL SM-35, cool stage) in fully hydrated hydrogels in order to identify any structural or morphological feature.

Swelling Tests 2-5 mg of dry sample was placed in 1 mL distilled water/PBS at pH 7.4 and 37° C. under mild shaking (following method of Roger P. Brown, Handbook of Polymer Testing: Physical Methods). Upon equilibrium with water, water uptake (WU) was calculated according to the following equation:

$$WU (\%) = \frac{W_s - W_d}{W_d} \times 100$$

wherein $W_s$ and $W_d$ are swollen and dry samples respectively. Swollen samples were blotted on blotting paper prior to measurement of $W_s$.

Compression Tests

Water-equilibrated hydrogel discs (ø0.8 cm) were compressed at room temperature with a compression rate of 3 mm·min$^{-1}$ (Instron 5544 UTM, ASTM standards). A 500 N load cell was operated up to sample break. The maximal compressive stress ($\sigma_{max}$) and compression at break ($\varepsilon_b$) were recorded, so that the compressive modulus (E) was calculated by fitting the linear region of the stress-strain curve. Four replicas were employed for each composition and results expressed as average±standard deviation.

Extract Cytotoxicity Assays

Cytotoxicity assays were conducted with L929 mouse fibroblasts and γ-sterilised photocrosslinked samples by the EN DIN ISO standard 10993-5. 0.1 mg of dry γ-sterilised sample was incubated in 1 mL cell culture medium (Dulbecco's Modified Eagle Medium) at 37° C. for 72 hours. Sample extract was collected and added to 80% confluent L929 cells. Dimethyl sulfoxide (DMSO) and virkon were used as negative controls. Double strength media was used as a positive control. Cell morphology was investigated after 48 hours cell culture using a transmitted light microscope in phase contrast mode (Zeiss, Germany).

Quantitative analysis of cell viability was carried out via LDH assay.

Properties of functionalised collagen and collagen based hydrogels were assessed and results are presented in Tables 1 and 2 which follow.

TABLE 1

Chemical and Structural Properties of Functionalised Collagens. Samples are coded as: XXXX YY. Whereby XXXX identifies the type of system, either GMA- or 4VBC based, while YY indicates the molar ratio of monomer with respect to the molar content in non-functionalized collagen

| Sample | Yield/ wt % | Free Lysine Content/μmol g$^{-1}$ | Total Vinyl Content/μmol g$^{-1}$ | Denaturation Temperature $(T_d)$/° C. |
|---|---|---|---|---|
| 4VBC 10 | — | 251 ± 43 | 42 ± 4 | 35 |
| 4VBC 25 | 86 | 255 ± 14 | 84 ± 3 | 37 |
| 4VBC 50 | 83 | 246 ± 13 | 99 ± 1 | — |
| 4 VBC 75 | — | 240 ± 49 | 132 ± 49 | 30 |
| GMA 10 | — | 293 ± 83 | 79 ± 83 | 37 |
| GMA 25 | 85 | 175 ± 21 | 96 ± 22 | 39 |
| GMA 50 | 81 | 172 ± 16 | 154 ± 14 | 37 |
| GMA 75 | — | 145 ± 1 | 228 ± 1 | 35 |
| MA 25 | 65 | 25 ± 2 | — | — |

TABLE 2

Thermo-Mechanical Properties of Collagen-Based Hydrogels. Samples are coded as CRT-XXXX YY, XXXX and YY have the same meaning as reported in table 1, while CRT is used here to identify the sample as collagen hydrogel instead of functionalized collagen.

| Sample | Shrinking Temperature/ ° C. | Equilibrium Water Uptake/wt % | Compressive Modulus/ kPa | Compressive Stress at Break/kPa | Compression at Break/kPa |
|---|---|---|---|---|---|
| Collagen | 67 ± 7 | 2863 ± 404 | — | — | — |
| CRT-4VBC 25 | — | 2770 ± 123 | 247 ± 103 | 35 ± 19 | 41 ± 6 |
| CRT-4VBC 50 | — | 2980 ± 660 | 226 ± 33 | 36 ± 13 | 35 ± 2 |
| CRT-GMA 10 | 64 ± 2 | 1956 ± 316 | — | — | — |
| CRT-GMA 25 | 79 ± 3 | 1230 ± 179 | 136 ± 57 | 28 ± 6 | 73 ± 3 |
| CRT-GMA 50 | 105 ± 1 | 707 ± 31 | 51 ± 35 | 12 ± 10 | 53 ± 13 |

Properties and characteristics of the functionalised collagens and collagen based hydrogels are further illustrated by the accompanying figures which also show a comparison with a commercially-available wound dressing product, Aquacel®.

Figure 2:
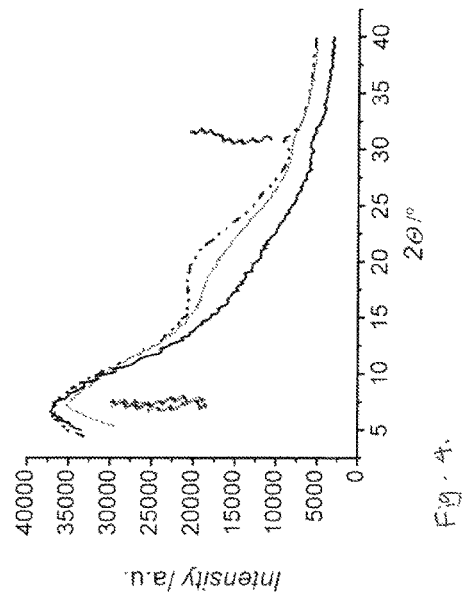
FIG. 2 shows an SEM picture of hydrogel CRT-GMA50 in hydrated conditions.
Figure 3:
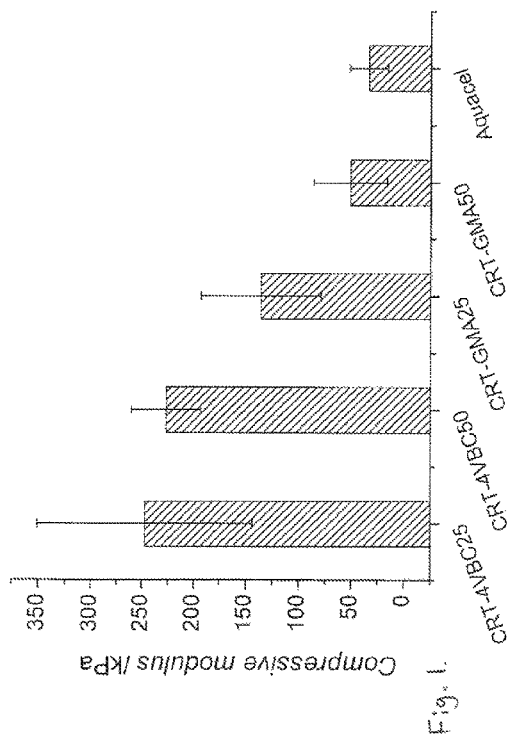
FIG. 3 shows water uptake of collagen hydrogels.
Figure 4:
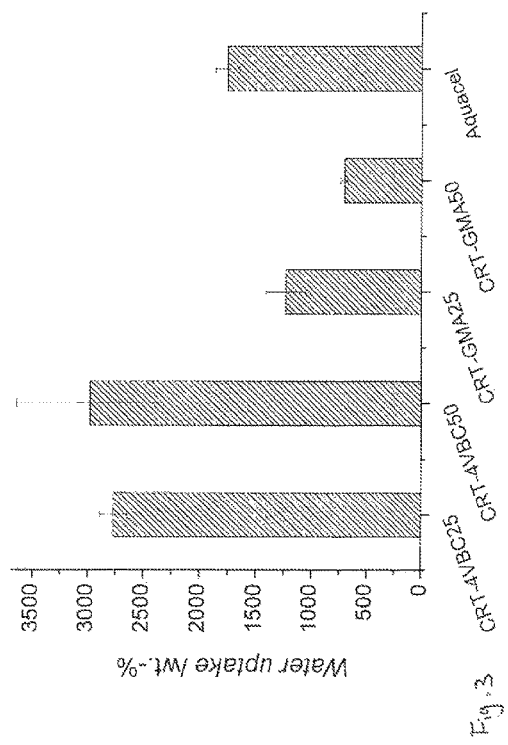
FIG. 4 shows a wide angle x-ray scattering spectra of dry collagen materials.

FIG. 1 shows compression modulus of collagen hydrogels (CRT-4VBC25, CRT-4VBC50, CRT-GMA25, CRT-GMA50) and Aquacel®, as commercially available wound dressing reference. FIG. 2 shows an SEM picture of hydrogel CRT-GMA50 in hydrated conditions. FIG. 3 shows water uptake of collagen hydrogels and Aquacel® and FIG. 4 shows a wide angle x-ray scattering spectra of dry collagen materials. In FIG. 4 there is shown wide-angle x-ray scattering of in-house isolated collagen from rat-tail (gray), photo-crosslinked GMA-functionalised collagen (solid black) and photo-crosslinked 4VBC-functionalised collagen (dashed back).

FIGS. 5, 6 and 7 show a L929 cell morphology picture following culture on exemplarily GMA-based hydrogel extract (FIG. 5) and cell culture medium (FIG. 6); vital cells cultured in contact with the hydrogel after 24 hours (FIG. 7). FIG. 8 shows LDH assay of cells cultured on sample extracts of GMA-based hydrogel.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of producing a collagen based polymeric material wherein the method comprises cross linking functionalised collagen and/or collagen derived molecules having one or more ethylenically unsaturated moieties,
   wherein the one or more ethylenically unsaturated moieties includes 4-vinylbenzyl chloride (4VBC).

2. A method according to claim 1, wherein the method comprises the steps of:
   (a) Functionalising collagen and/or collagen derived molecules by the addition of one or more moieties comprising a vinyl group; and
   (b) Crosslinking of the functionalised collagen and/or collagen derived molecules of (a).

3. A collagen based composition comprising a functionalised collagen and/or collagen derived molecule, wherein the collagen and/or collagen derived molecule is functionalised by addition of one or more ethylenically unsaturated moieties wherein the one or more ethylenically unsaturated moieties includes 4-vinylbenzyl chloride (4VBC).

4. A method of producing a collagen based polymeric material according to claim 1, wherein the material is produced in the form of one or more fibres and/or one or more filaments and/or one or more films and/or one or more gels and wherein the method comprises the steps of:
   (a) Functionalising collagen and/or collagen derived molecules with the one or more ethylenically unsaturated moieties;
   (b) Combining the functionalised collagen and/or collagen derived molecules with a vehicle; and
   (c) Wet spinning the functionalised collagen and/or collagen derived molecules.

5. A method according to claim 1, wherein the material is produced in the form of one or more fibres and/or one or more filaments and/or one or more films and/or one or more gels and wherein the method comprises the steps of:
   (a) Functionalising collagen and/or collagen derived molecules with the one or more ethylenically unsaturated moieties;
   (b) Combining the functionalised collagen and/or collagen derived molecules with a vehicle; and
   (c) Wet spinning the functionalised collagen and/or collagen derived molecules; and
   wherein a photoinitiator is added during or after steps (b) and/or (c).

6. A method according to claim 4, wherein the formed collagen fibres and/or filaments have a diameter of between about 0.01 µm and 50 µm.

7. A method according to claim 1, further comprising:
   forming a web, a tow, a yarn, and/or a nonwoven of functionalised collagen fibres and/or filaments and/or films,
   wherein a pore size of the web, the tow, the yarn, and/or the nonwoven of functionalised collagen fibres and/or filaments and/or films is between about 5 µm and 350 µm.

8. A method according to claim 1, wherein the material or composition comprises functionalised collagen which has a preserved triple helical structure.

9. A method according to claim 1, wherein [4-(2-hydroxyethoxy)phenyl-(2-hydroxy-2-propyl)ketone] (Irgacure® 2959) is used as a photoinitiator for cross-linking.

10. A method according to claim 1, wherein a degree of functionalisation of the collagen is controllable and is variable between 5 mol % and 100 mol %.

11. A method according to claim 1, wherein a compressive modulus (E) of the material is between 50 kPa and 300 kPa.

12. A method according to claim 1, wherein a swelling ratio of the material is higher than at least 100 wt %.

13. A method according to claim 1, wherein a degradation time of the material is higher than at least 3 days and wherein a denaturation temperature of the material is between about 60° C. and 90° C.

14. A method according to claim 1, wherein the one or more ethylenically unsaturated moieties includes a combination of 4-vinylbenzyl chloride (4VBC) and glycidyl methacrylate (GMA).

15. A method according to claim 1, wherein the one or more ethylenically unsaturated moieties includes a combination of 4-vinylbenzyl chloride (4VBC) and methacrylic anhydride (MA).

16. A method according to claim 5, wherein the photoinitiator is [4-(2-hydroxyethoxy)phenyl-(2-hydroxy-2-propyl)ketone] (Irgacure® 2959).

* * * * *